United States Patent [19]

Amey

[11] Patent Number: 4,935,521

[45] Date of Patent: Jun. 19, 1990

[54] PREPARATION OF 3-PICOLINE

[75] Inventor: Ronald L. Amey, Wilmington, Del.

[73] Assignee: E. I. Du Pont de Nemours and Company, Wilmington, Del.

[21] Appl. No.: 334,241

[22] Filed: Apr. 6, 1989

[51] Int. Cl.[5] .............. C07D 213/127; C07D 213/133
[52] U.S. Cl. .................... 546/251; 546/250; 546/252
[58] Field of Search ............... 546/251, 252

[56] References Cited

U.S. PATENT DOCUMENTS 4,086,237  4/1978  Daum et al. ............... 546/252

FOREIGN PATENT DOCUMENTS 0654576  2/1986  Switzerland ............... 546/251

Primary Examiner—Alan L. Rotman

[57] ABSTRACT

Preparation of 3-picoline from 2-methylglutaronitrile in which the by-products, i.e., 3-methylpiperidine, 2-amino-3-picoline, and 2-amino-5-picoline are recycled and converted to 3-picoline.

6 Claims, 1 Drawing Sheet

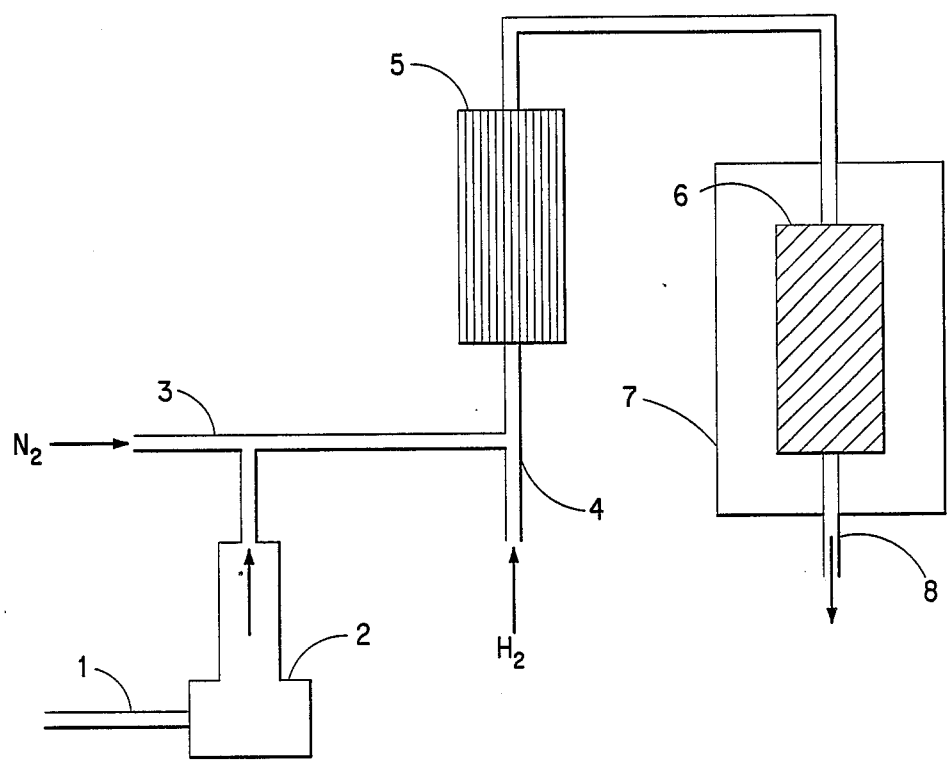
FIGURE

PREPARATION OF 3-PICOLINE

Field of the Invention

This invention relates to the preparation of 3-picoline (also called 3-methylpyridine and beta-picoline) from 2-methylglutaronitrile. More particularly this invention relates to the production of 3-picoline from by-products of the production of 3-picoline from 2-methylglutaronitrile. Even more particularly this invention relates to the production of 3-picoline from a reaction mixture containing 3-methylpiperidine, 2-amino-3-picoline and 2-amino-5-picoline, or from 2-amino-3-picoline, or 2-amino-5-picoline.

Background of the Invention 3-picoline is an intermediate in the production of niacin, one of the B vitamins. It is also useful as a solvent.

U.S. Pat. No. 4,051,140 assigned to Lummus Company discloses the preparation of 3-picoline from 3-methylpiperidine.

EPO Patent No. 0,062,264 assigned to Lonza AG discloses a process for the production of 3-picoline from 2-methylglutaronitrile using a platinum or palladium catalyst.

Swiss Patent No. 654,576 assigned to Lonza AG discloses the manufacture of 3-picoline by the vapor phase reaction of 2-methylglutaronitrile with hydrogen in the presence of a platinum or palladium supported catalyst.

Summary of the Invention

This invention is a process for the production of 3-picoline by reacting a mixture of 3-methylpiperidine, 2-amino-3-picoline, and 2-amino-5-picoline in the vapor phase with hydrogen in the presence of a supported catalyst selected from the class consisting of platinum and palladium metal catalysts at a temperature of 225° to 325° C. This mixture of 3-methylpiperidine, 2-amino-3-picoline, and 2-amino-5-picoline may be obtained by the reaction of 2-methylglutaronitrile with hydrogen over a supported catalyst selected from the class consisting of platinum metal deposited on a solid support, and palladium metal deposited on a solid support. This reaction may also be carried out at a temperature of about 225° to 325° C. The reaction of 2-methylglutaronitrile under these conditions also produces 3-picoline. The 3-picoline is separated from the reaction product mixture, and the other components are then reacted to produce 3-picoline.

The catalyst used in the reaction of 2-methylglutaronitrile may be the same catalyst as used in the reaction of 3-methylpiperidine, 2-amino-3-picoline, and 2-amino-5-picoline.

Description of the Drawing

The drawing is a simplified schematic flow diagram of the process for producing 3-picoline from 2-methylglutaronitrile.

Detailed Description of the Invention

The present invention is based on the discovery that a mixture of 3-methylpiperidine, 2-amino-3-picoline, and 2-amino-5-picoline may be used as a starting material for the production of 3-picoline, and that 2-amino-3-picoline or 2-amino-5-picoline may also be used as such a starting material. In particular it was unknown prior to the present invention that 2-amino-3-picoline and 2-amino-5-picoline could be de-aminated to produce 3-picoline. The production of 3-picoline from 2-methylglutaronitrile and the co-production of 3-picoline and 2-amino-3-picoline and 2-amino-5-picoline is not an entirely satisfactory process because too much starting material ends up as the undesired by-product. But the discovery that these by-products can be converted to 3-picoline makes the process much more commercially attractive.

The process of this invention is carried out in the vapor phase over a catalyst selected from the class consisting of supported platinum metal catalysts and supported palladium metal catalysts. Suitable catalyst supports include: alumina, silica, alumina/silica mixtures, titania, carbon, aluminum fluoride, and kieselguhr. The amount of metal on the support should be in the range of about 0.5 to 5% by weight. Preferably the catalyst has a high surface area, and the support is gamma-alumina, i.e. $\gamma$-Al$_2$O$_3$.

The process of the invention can be run in a fixed bed reactor or in a fluidized bed reactor. In a fixed bed reactor the catalyst may be in the form of pellets having diameters of about ⅛ inch or greater. In a fluidized bed, the catalyst may have a particle size of between 5 and 75 microns.

In a preferred embodiment, the process of the present invention includes the reaction of 2-methylglutaronitrile over the supported catalyst to form a mixture of 3-picoline, 3-methylpiperidine, 2-amino-3-picoline, and 2-amino-5-picoline. This reaction mixture is then separated to recover the 3-picoline, and the remaining portion of the mixture is recycled to the catalyst. The recycled components of the mixture may be, and preferably are combined with "fresh" 2-methylglutaronitrile and hydrogen, and the mixture reacted in the presence of the catalyst.

The reaction takes place in the presence of hydrogen. Hydrogen should be present in the mixture of vapor fed to the catalyst in a mole ratio of hydrogen to 2-methylglutaronitrile, or 2-methylglutaronitrile equivalent, in the range of about 4 to 1 to about 10 to 1. (To calculate the 2-methylglutaronitrile equivalence, convert moles of the feed, for example 3-methylpiperidine to the number of moles of 2-methylglutaronitrile needed to generate that product and then base the number of moles of hydrogen on the number thus obtained.)

It is often desirable to have an inert diluent present in the vapor fed to the catalyst. Nitrogen is suitable and is relatively inexpensive.

The FIGURE shows the laboratory reactor that may be employed to carry out the process of the invention. Organic feed 1, (for example, 2-methylglutaronitrile, or a mixture of 2-methylglutaronitrile, 3-methylpiperidine, 2-amino-3-picoline, and 2-amino-5-picoline) is provided through pump 2 and combined with nitrogen stream 3 and hydrogen stream 4, and passes into vaporizer 5, and then into reactor 6 containing the supported catalyst, and the reaction products leave the reactor through conduit 8.

The products are then separated, i.e., 3-picoline recovered from the reaction products, and the remaining components are recycled to pump 2 where they are combined with additional 2-methyl glutaronitrile and hydrogen, and this mixture is then passed again through vaporizer, reactor, etc.

EXAMPLE 1

The equipment employed is like that shown in the FIGURE. The reactor had an outer diameter of ½ inch, a wall thickness of 0.0625 inch, an internal diameter of 0.437 inch and a length of 6 inches and was made of stainless steel. All lines after the vaporizer were heated. The vaporizer was heated to a temperature of 300° C. The catalyst was 2% palladium on gamma-alumina of high surface area in the form of cylinders ⅛ inch in diameter and ⅛ inch long (Engelhard Lot #118-7-DD-46). About 20 to 25 grams of catalyst was put into the reactor. Each end of the reactor was fitted with a layer of quartz wool about 0.125 to 0.25 inches thick. The reactor was also heated to 300° C. The feed was pure 2-amino-3-picoline, 1.2 ml per hour, 2 liters per hour of hydrogen, and 0.5 liters per hour of nitrogen. Samples were collected after 1 hour, after 2 hours, and after 3 hours. The results are tabulated below:

| Sample | 3-p%* | 3-mp%** | 2-a-3-p%*** |
|---|---|---|---|
| 1 hour | 13 | 36 | 16.5 |
| 2 hour | 11 | 31 | 45 |
| 3 hour | 11 | 22 | 53 |

*3-picoline
**3-methylpiperidine
***2-amino-3-picoline

EXAMPLE 2

Using the same equipment set-up as example 1 and a 2% palladium on gamma Al$_2$O$_3$: catalyst (Engelhard Lot #C-9952) the temperature of the reactor was 250° C. and the temperature of the vaporizer was 275° C. The feed was 2.4 ml per hour of a 65/35 volume per volume mixture of 3-methylpiperidine and 2-amino-3-picoline; with 2 liters per hour of hydrogen and 0.5 liters per hour of nitrogen. Samples were taken every hour for seven hours and the results are shown in the table below:

| Sample | 3-p%* | 3-mp%** | 2-a-3-p%*** |
|---|---|---|---|
| 1 hour | 15 | 81 | 1 |
| 2 hour | 16 | 81 | 1 |
| 3 hour | 18 | 78 | 2 |
| 4 hour | 20 | 77 | 2 |
| 5 hour | 21 | 74 | 3 |
| 6 hour | 19 | 75 | 5 |
| 7 hour | 18 | 77 | 4 |

*3-picoline
**3-methylpiperidine
***2-amino-3-picoline

EXAMPLE 3

Using the equipment set-up shown in the FIGURE, and the catalyst of Example 1 the vaporizer was run at 275° C. and the reactor also at 275° C. The feed was a mixture of 50% 3-methylpiperidine, 25% 2-amino-3-picoline, and 25% 2-amino-5-picoline (2.4 ml per hour), two liters of hydrogen per hour and 0.5 liters of nitrogen per hour. The results are set forth in the table below:

| Sample | 3-p%* | 3-mp%** | 2-a-3p%*** and 2-a-5p%**** |
|---|---|---|---|
| 1 hour | 73.5 | 13.2 | 11.3 |
| 2 hour | 69.8 | 15.6 | 12.6 |
| 3 hour | 56.9 | 25.7 | 15.4 |
| 4 hour | 57.3 | 26.5 | 14.2 |

*3-picoline
**3-methylpiperidine
***2-amino-3-picoline
****2-amino-5-picoline

EXAMPLE 4

Using the equipment set-up as shown in the FIGURE, the reactor and the vaporizer were operated at 275° C. The catalyst was the same as previously described in Example 1 and the feed was 80% of a 98.5% 2-methylglutaronitrile and 1.5% 2-ethylsuccinonitrile mixture and 10% 3-methylpiperidine, 5% 2-ethylsuccinonitrile mixture and 10% 3-methylpiperidine, 5% 2-amino-3-picoline, and 5% 2-amino-5-picoline (2.4 ml per hour). Hydrogen was fed at 2 liters per hour and nitrogen fed at 0.5 liters per hour. The results are shown below:

| Sample | 3-p%* | 3-mp%** | 2-a-3-p%*** and 2-a-3-p%**** |
|---|---|---|---|
| 1 hour | 56.1 | 19.0 | 18.2 |
| 2 hour | 55.8 | 18.7 | 22.7 |
| 3 hour | 50.0 | 22.7 | 24.9 |
| 4 hour | 50.6 | 20.5 | 21.3 |

*3-picoline
**3-methylpiperidine
***2-amino-3-picoline
****2-amino-5-picoline

I claim:

1. A process for the preparation of 3-picoline from 2-methylglutaronitrile which comprises reacting in the vapor phase 2-methylglutaronitrile with hydrogen over a supported catalyst selected from the class consisting of platinum metal deposited on a solid support, and palladium metal deposited on a solid support, at a temperature of 225° C. to 325° C., separating from the product mixture (a) 3-picoline, and (b) a mixture comprising 3-methylpiperidine, 2-amino-3-picoline, and 2-amino-5-picoline, and reacting this separated mixture in the vapor phase in the presence of hydrogen and a supported palladium metal or a supported platinum metal catalyst at a temperature of 225® to 325° C. to produce 3-picoline.

2. The process of claim 1 in which the mixture of 3-methylpiperidine, 2-amino-3-picoline, and 2-amino-5-picoline is recycled to the catalyst originally employed in the reaction of 2-methylglutaronitrile.

3. A process for the preparation of 3-picoline which comprises reacting in the vapor phase a mixture of 3-methylpiperidine, 2-amino-3-picoline, and 2-amino-5-picoline with hydrogen in the presence of a supported catalyst selected from the class consisting of platinum and palladium metal catalysts at a temperature of 225° C. to 325° C.

4. The process of claim 3 in which 2-methylglutaronitrile is co-fed to the catalyst simultaneously with the mixture.

5. A continuous process for the preparation of 3-picoline which comprises reacting in the vapor phase, continuously fed streams of 2-methylglutaronitrile and hydrogen in the presence of a supported catalyst selected from the class consisting of platinum metal and palladium metal catalysts at a temperature of 225° C. to 325° C., recovering a product stream containing a mixture of 3-picoline, 3-methylpiperidine, 2-amino-3-picoline, and 2-amino-5-picoline, separating 3-picoline from the mixture, and recycling the remaining components of the mixture to the supported catalyst, and reacting these remaining components in the presence of hydrogen to product 3-picoline.

6. A process of preparing 3-picoline which comprises reacting 2-amino-3-picoline or 2-amino-5-picoline or mixtures thereof with hydrogen at a temperature of 225° to 325° C. in the presence of a catalyst selected from the class consisting of supported palladium metal and supported platinum metal.

* * * * *